(12) United States Patent
Ferek-Petric

(10) Patent No.: US 6,473,638 B2
(45) Date of Patent: Oct. 29, 2002

(54) MEDICAL DEVICE GUI FOR CARDIAC ELECTROPHYSIOLOGY DISPLAY AND DATA COMMUNICATION

(75) Inventor: Bozidar Ferek-Petric, Zagreb (CR)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/746,230

(22) Filed: Dec. 21, 2000

(65) Prior Publication Data

US 2001/0044586 A1 Nov. 22, 2001

Related U.S. Application Data

(60) Provisional application No. 60/173,065, filed on Dec. 24, 1999.

(51) Int. Cl.⁷ .............................................. A61B 5/044
(52) U.S. Cl. ..................................................... 600/523
(58) Field of Search ............................ 600/523, 509, 600/510

(56) References Cited

U.S. PATENT DOCUMENTS

| | | | | |
|---|---|---|---|---|
| 4,142,533 A | * | 3/1979 | Brownlee et al. | |
| 4,527,567 A | * | 7/1985 | Fischler et al. | |
| 4,596,255 A | * | 6/1986 | Snell et al. | |
| 4,791,936 A | * | 12/1988 | Snell et al. | |
| 4,809,697 A | * | 3/1989 | Causey, III et al. | |
| 4,958,632 A | * | 9/1990 | Duggan | |
| 5,372,607 A | * | 12/1994 | Stone et al. | |
| 5,421,830 A | * | 6/1995 | Epstein et al. | |
| 5,447,164 A | * | 9/1995 | Shaya et al. | |
| 5,713,937 A | * | 2/1998 | Nappholz et al. | |
| 5,716,384 A | * | 2/1998 | Snell | |
| 5,722,999 A | * | 3/1998 | Snell | |
| 5,724,985 A | * | 3/1998 | Snell et al. | |
| 5,833,623 A | * | 11/1998 | Mann et al. | |
| 5,843,138 A | * | 12/1998 | Evers et al. | |
| 5,891,178 A | * | 4/1999 | Mann et al. | |
| 5,954,666 A | * | 9/1999 | Snell | |
| 6,088,618 A | * | 7/2000 | Kerver | |

FOREIGN PATENT DOCUMENTS

| EP | 0 444 251 A2 | 4/1991 | ........... G06F/3/033 |
|---|---|---|---|
| EP | 0 592 921 A1 | 4/1994 | ........... G05B/23/02 |

* cited by examiner

Primary Examiner—Scott M. Getzow
(74) Attorney, Agent, or Firm—Girma Wolde-Michael

(57) ABSTRACT

An interactive graphical user interface (GUI) is implemented to display virtual static and animated cardiac electrophysiology and implanted medical device information. The GUI is structured in a layered format to display a subset of display means relating to further details. The invention also enables access and transfer of the display and associated information via a network system preferably web-enabled to use the Internet.

17 Claims, 6 Drawing Sheets

MEDICAL DEVICE GUI FOR CARDIAC ELECTROPHYSIOLOGY DISPLAY AND DATA COMMUNICATION

CROSS-REFERENCE TO RELATED APPLICATIONS

This application claims the benefit of U.S. Provisional Application No. 60/173,065 filed Dec. 24, 1999. The specification and drawings of the provisional application are specifically are incorporated by reference herein.

FIELD OF THE INVENTION

The present invention generally relates to graphical user interface (GUI) displayable on a medical device or instrument such as a programmer to provide a visual/animated display of patient organs including pictorial representation of implanted medical devices (IMDs) in a patient. Specifically, the invention relates to a communication means with the IMDs in a patient on a real time basis to evaluate, monitor and dispense therapy and clinical care as needed. Preferably, an interface medical instrument such as a programmer is used to display information relating to the IMDs including operating parameters and status. The system further enables remote transfer of information and communication between instruments at the patient's station or home and caregivers at different locations. using web-enabled network systems such as the Internet.

BACKGROUND OF THE INVENTION

The present invention is compatible and complementary with the elements disclosed in the following pending applications: "Medical System Having Improved Telemetry," filed Jul. 19, 1999, Ser. No. 09/356,340; "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/429; "Apparatus and Method for Remote Self-Identification of Components in Medical Device Systems," filed Oct. 29, 1 999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881 "Implantable Medical Device Programming Apparatus Having An Auxiliary Component Storage Compartment," filed Nov. 4, 1999, Ser. No. 09/433,477; "Remote Delivery Of SoftwareBased Training For Implantable Medical Device Systems," filed Nov. 10, 1999, Ser. No. 09/437,615; "Apparatus and Method for Remote Therapy and Diagnosis in Medical Devices Via Interface Systems," filed Dec. 14, 1999, Ser. No. 09/460,580; "Virtual Remote Monitor, Alert, Diagnostics and Programming For Implantable Medical Device Systems" filed Dec. 17, 1999, Ser. No. 09/466,284; "Instrumentation and Software for Remote Monitoring and Programming of Implantable Medical Devices (IMDs), filed Dec. 21, 1999, Ser. No. 60/172,937; "Application Proxy For Telecommunication-enabled Remote Medical Access Instruments," filed Dec. 23, 1999, Ser. No. 60/173,081; "Information Network Scheme For Interrogation Of Implantable Medical Devices (IMDs)," filed Dec. 24, 1999, Ser. No. 60/173,064; "Medical Device GUI For Cardiac Electrophysiology Display And Data Communications," filed Dec. 24, 1999, Ser. No. 60/173,065; "Integrated Software System For Implantable Medical Device Installation And Management," filed Dec. 24, 1999, Ser. No. 60/173,082; "Dynamic Bandwidth Monitor And Adjuster For Remote Communications With A Medical Device," filed Dec. 24, 1999, Ser. No. 60/173,083 "Large-Scale Processing Loop For Implantable Medical Devices (IMDs)," filed Dec. 24, 1999, Ser. No. 60/173,079; "Chronic Real-Time Information Management Systems For Implantable Medical Devices (IMDs)," filed Dec. 24, 1999, Ser. No. 60/173,062; "Automatic Voice and Data Recognition For Medical Device Instrument Systems," filed Dec. 24, 1999, Ser. No. 60/173,071 "Central Switchboard to Facilitate Remote Collaboration With Medical Instruments," filed Dec. 24, 1999, Ser. No. 60/173,080; which are all incorporated by reference herein in their entireties.

A technology based health care system that fully integrates the technical and social aspects of patient care and therapy should be able to flawlessly connect the client with care providers, irrespective of separation distance or location of the participants. While clinicians will continue to treat patients in accordance with accepted modern medical practice, development in communications technology are making it evermore possible to provide medical services in a time and place in an independent manner.

Prior art methods of clinical services are generally limited to in-hospital operations. For example, if a physician needs to review the performance parameters of an implantable medical device in a patient, it is likely that the patient has to go to the clinic. Further, if the medical conditions of a patient with an implantable medical device warrant a continuous monitoring or adjustment of the device, the patient would have to stay in a hospital indefinitely. Such a continued treatment plan poses both economic and social problems. Under the exemplary scenario, as a segment of the population with implanted medical devices increases, many more hospitals/clinics, including service personnel, will be needed to provide in-hospital service for the patients, thus escalating the cost of health care. Additionally, the patients will be restricted and inconvenienced by the need to either stay in the hospital or make very frequent visits to a clinic.

Yet another condition of the prior art practice requires that a patient visit a clinic center for occasional retrieval of data from the implanted medical device to assist the operation of the device and gather patient history for both clinical and research purposes. Such data is acquired by having the patient in a hospital/clinic to upload the stored data from the implantable medical device. Depending on the frequency of data collection, this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice, it is an industry-wide standard to keep an accurate record of past and contemporaneous procedures relating to an implantable medical device uplink with, for example, a programmer. It is required that the report contain identification of all the medical devices and instruments involved in any interactive procedure. Specifically, all peripheral and major devices and instruments that are used in downlinking to the IMD, need to be reported.

IMDs, medical instruments, programmers and related medical devices are distributed throughout the world.

Further, the number of people with implanted medical devices has been increasing steadily over the last few years. Thus, it is desireable to have a high efficiency communication system that would provide display and data communications with medical devices. A further limitation of the prior art relates to the management of multiple implanted medical devices in a single patient. Advances in modern therapy and treatment have made it possible to implant a number of devices in a patient. For example, IMDs such as a defibrillator or a pacer, a neural implant, a drug pump, a physiology monitor, and various other IMDs may be implanted in a single patient. To successfully manage the operations and assist the performance of each device in a patient with multi implants requires continuous updates and monitoring of the devices. Further, it may be preferred to have an operable communication between the various implants to provide a coordinated clinical therapy to the patient. Thus, there is a need to monitor the IMDs, including the programmer and instruments, on a regular if not continuous basis, to ensure optimal patient care. In the absence of other alternatives, this imposes a great burden on the patient if a hospital or clinic is the only center where the necessary follow-up and data communications could be made to enable upgrade evaluation and digestion of the IMDs. Further, even if feasible, the situation would require the establishment of multiple service areas or clinic centers to support the burgeoning number of multi-implant patients worldwide.

Accordingly, it is vital to have a user interface device or instrument that would enable remote communications and display of implanted medical device data. Specifically, it would be desireable to connect to a remote expert data center, a remote wavebase data center, or a remote data center—all these terms are alternate equivalents of each other as used herein. The ability to transfer information between the IMDs and the remote center is highly desirable in order to dispense therapy and clinical care on real time basis.

PCT Publication WO00/30712 to Nova, Richard C. et al, discloses a visual and aural user interface for an automated external defibrillator (AED) designed for use by a rescuer, with minimal or no training, during a medical emergency. The AED implements a user interface program which guides the rescuer through operation of the AED and application of CPR and defibrillation therapy to a patient by displaying a series of visual instructions on a graphic display or other visual output device. The system also provides additional aural instructions via a speaker or other aural output device. The rescuer merely needs to press a start button to initiate operation of the AED and begin CPR and defibrillation instructions.

U.S. Pat. No. 5,447,164 to Shaya et al, discloses an interactive medical information display system and method for displaying user definable patient events. Specifically, the invention discloses an interactive medical information display system that includes a mechanism for acquiring physiological parameters from a patient and the mechanism for storing the parameters in a real time data base. In addition, the system includes a mechanism for users to define event types in an event definition language, and a mechanism for users to modify existing event types. Users may select a set of event types for display and an event generator accesses the data base to monitor the physiological parameters in order to detect event occurrences as defined by the event types. A display mechanism displays the event occurrences and provides users with the ability to select event occurrences randomly or sequentially. Upon selection, other information is displayed.

U.S. Pat. No. 4,958,632 to Duggan discloses an adaptable digital computer controlled cardiac pacemaker. The invention discloses a multi-mode adaptable, implantable pacemaker, including a microprocessor and memory programmed or capable of being programmed with a variety of processes for stimulating the patient's heart and/or for sensing and transmitting to a device external of the patient's body. Specifically, various conditions or activities of the patient's heart or conditions of the implanted medical device are sensed or transmitted to the external device. The pacemaker is capable of transmitting these signals via link such as RF or acoustical link to an external monitoring apparatus. The external apparatus may transmit code signals to be received by the pacemaker whereby the pacemaker's memory may be reprogrammed dependent upon change of the patient's condition.

U.S. Pat. No. 4,142,533 to Brownlee et al, discloses a monitoring system for cardiac pacers. The invention describes a system for telemetering and monitoring the functions of an implanted pacemaker as well as controlling the testing of the functions from a remotely located central facility. The invention claims capabilities of directly and simultaneously transmitting from the pacer electrical signals indicative of multiple pacer functions such as pacer rate, cell voltage, refractory period, heart rate, pacer inhibited R-Wave level and sensing margin, sensing circuits and other component failure, cardiac electrode lead break and hermetic integrity. The indicator signals are picked up at the patient's location for local analysis and/or for telephonic communication to a remote central monitoring station. The central station may control testing of the pacemaker functions by transmitting command signals back telephonically for coupling through cooperating external and implanted inductances or magnetically controlled switches to the implanted pacer circuitry.

U.S. Pat. No. 4,527,567 to Fischler et al describes a method and apparatus for automatically evaluating the quality of the performance of a cardiac pacing system. Specifically the invention discloses an extracorporeal self-contained online beat to beat pacemaker function analyzer for automatically evaluating and indicating the quality of performance of cardiac pacing systems implanted in place for routine examination of ambulatory patients. Further, long term surveillance of hospitalized patients and examination of ECG traces of remote technical patients transferred by telephone or radio to central follow-up stations is also disclosed. The pacemaker function analyzer provides a comprehensive examination of a synchronous demand and demand hysterisis testmakers of all makes including the state of the pacemaker's battery, the intactness of the electronic circuitry and of the electrodes and of the proper location of the electrodes in the heart.

U.S. Pat. No. 4,596,255 to Snell et al, discloses apparatus for interpreting and displaying cardiac events of a heart connected to a cardiac pacing means. The system includes a display unit, a telemetry head, a first interpreting means connected to the telemetry head, a second interpreting means connected to a number of ECG electrodes having paddles at said digital end by electrical conduits, a control means connected to the first and second interpreting means and respectively, a multi-section memory means with means connected to said control means. Further, a digital to analog converter connected to a memory system, a printing means and a logic system that is in turn connected to the display means. U.S. Pat. No. 4,791,936 to Snell et al, discloses, in addition to the disclosures in U.S. Pat. No. 4,596,255, a process in which information telemetered from the implanted pacing means is separated in viable sets of data pertaining to a prescribed function such as atrial events, ventricular events, pacemaker timed events, sensor events and the like. Skin ECG information may also be received through another interpreting means in addition to pacemaker telemetered data. Parallel processing channels are employed to process all the received data while maintaining synchronization therebetween. Memory means allows the processed data to be stored for subsequent printouts through a digital to analog converter and printer or to be displayed on a display monitor. The display monitor is controlled by display logics that includes the capability to simultaneously display a number of selected data sets while maintaining the synchronization therebetween. The system also allows displayed events to be identified with unique markers, or synchronized with displayed time intervals associated with the operation of the pacemaker.

U.S. Pat. No. 4,809,697 to Causey, III et al discloses interactive programming and diagnostic system for use with implantable pacemakers. The invention describes an analyzer programmer system for use with an implantable medical device. The system is claimed to facilitate non-invasive communications with the implanted device to make analysis of the operation of the implanted device easier to understand and perform. Further conventional processor means is used for processing a sequence of stored instructions. Programmed intervals to be sent to the implantable device are displayed by the system in tabular form, or as skilled time lines or bars, with each separate interval beginning and ending in proper time sequence, thereby providing a prediction of the expected performance. The system also includes telemetry head means for sending and receiving control and data signals to and from the implanted medical device. The telemetry head includes processing circuitry claimed to simplify the other circuitry needed in order to effectuate such communication.

U.S. Pat. No. 5,713,937 to Nappholz et al, discloses a pacemaker programmer menu with selectable real or simulated implant data graphics. The invention discloses a graphic user interface for a cardiac implant such as an implant programmer which includes image generators for generating multiple images on the screen. Each image responding to a presentation of a parameter related to the operation of the implant or a cardiac function and an indicia generator for superimposing on the images indicative of the interrelation between the parameters. The indicia allows the user to obtain a clear understanding and appreciation of the cause and effect rules between various cardiac parameters and/or functions. The parameters or functions could be actual, that is obtained from the implanted or the patient heart or they can be simulated to provide the user an indication of how the pacemaker will operate under these simulated conditions parameters.

U.S. Pat. No. 5,724,985 to Snell et al, discloses a user interface for an implantable medical device using an integrated digitizer display screen. The invention relates to an apparatus and method for improved interface for communicating with implanted medical devices. An integrated digitizer display screen and an digitizer pen serve as a primary input to this device to a tablet computer adapted to receive real time and stored medical data. The pen is used to select programming options by tapping portions of the digitizer based on visual images on the display. Additionally, the pen may be used to manipulate the medical data through the use of gestures or be used to enter free form annotations concerning the medical data. An additional aspect of the invention includes a user interface for use of a questionnaire card to input information into the tablet computer by tapping the pen on the marked answers on the questionnaire card.

U.S. Pat. No. 5,372,607 to Stone et al, discloses a method and apparatus for monitoring pacemaker intervals. In accordance with the invention, a pacemaker is provided which is capable of obtaining and storing information about a patient's cardiac function, and about a pacemaker's operation during a brief exercise interval. The data collected includes information about the number of cardiac events during each two second interval of the exercise as well as a percentage of paced events during each two second interval. In this manner, data reflecting output of the pacemaker activity is collected. The invention is operable in conjunction with an external programming/processing unit that receives the stored data after the exercise test is concluded. The data is processed and presented on the programmer's screen in a manner that enables the clinician to readily assimilate and observe the effects of hypothetical changes in retrosponse programming in the pacemaker. Additionally, the clinician is able to observe the program's AV rated adaptation profiles in conduction with the patient's actual AV performance, and compares this data with an AV profile from a typical healthy heart.

U.S. Pat. No. 5,716,324 to Snell, describes a method and system for organizing, viewing and manipulating information in implantable device programmers. In accordance with this invention, a method and system are provided for organizing, viewing and manipulating information in an implantable device programmer. The information includes programmable parameters which are divided into key parameters in subordinate parameters. Each key parameters has one or more associated subordinate parameters that are displayed when the user selects the key parameter. These parameters are not displayed when a different key parameter is selected. Subordinate parameters can be made sticky by the user. A sticky subordinate parameter is displayed regardless of whether or not the user has selected its associated key parameter. Certain parameters are linked so that when the user selects any one of the linked parameters, all linked parameters are displayed. Certain parameters are designated as inactive because of interactions with other parameters.

U.S. Pat. No. 5,722,999 to Snell, discloses a system and method for storing and displaying historical medical data measured by an implantable medical device. The invention relates to a system invented for acquiring medical data integrating recently acquired medical data with previously acquired medical data, storing the integrated medical data and displaying the integrated medical data to a medical practitioner in a convenient format. The recently acquired medical data are integrated with historical medical data in an implantable medical device programmer. The data may be initially displayed in graphical and text formats during a patient's follow-up visit. The historical medical data may be stored in the programmer or the implantable medical device or both. Medical data may include physiological data pertaining to the patient's medical condition, parametric data pertaining to the operational characteristics of the implanted medical device, identification data including patient's background information and comments, including the medical practitioner's comments.

U.S. Pat. No. 5,833,623 to Mann et al, relates to a system and method for facilitating rapid retrieval and evaluation of diagnostic data stored by an implantable medical device. The invention relates to an implantable medical device programmer that includes a variety of features for allowing the clinician to perform an automated and customized follow-up examination of a patient having an implanted cardiac implantable device. A custom protocol feature of the programmer allows the clinician to prespecify and then semi-automatically follow an ordered sequence of protocol steps. Each protocol step preferably involves the interrogation of the implanted medical device in the display by the programmer of associated implantable device data, such as for example, heart rate histogram or the results of a ventricular capture test. When the clinician initiates a custom protocol, the programmer automatically retrieves all of the diagnostic data records of the protocol in the protocol order. This automatic retrieval is performed in the background allowing the clinician to begin viewing the initial diagnostic data records of the protocol while the other items are being retrieved.

U.S. Pat. No. 5,421,830 to Epstein et al, describes a programming system having means for recording and analyzing a patient's cardiac signal. Specifically, the invention relates to a programming system that allows a physician or medical personnel to optimize the settings of various arrhythmia detection criteria and/or parameters related to hemodynamic performance to be programmed into the implanted cardiac stimulating device. The programming system may play back the recorded signals to test the detection criteria and hemodynamic performance and may simulate the response of the device to the cardiac signal. Alternatively, the programming system may relay back an artificially created or previously stored cardiac signal for test purposes. As a result, the recorded signal may be played back repeatedly without unnecessarily stressing the patient's heart. Additionally, the programmer may suggest a specific arrhythmia detection criteria and therapies to a physician based on an analysis of a patient's arrhythmia.

U.S. Pat. No. 5,843,148 to Evers et al, discloses a pacemaker system with enhanced programmable modification capacity. Specifically, the invention relates to a pacemaker system that provides flexibility in reprogramming of the control software or a program which is controlling an implanted pacemaker. The system includes an external programmer device that is capable both of programming the implanted device in a conventional way and also downloading new control software to the implatned device. In applications where there are more than one pacemakers, the invention enables identifying the type of pacemaker within the group and a set of permissions data representative of different types within the group to which it is permitted to be programmed. Upon interrogating the implanted device, the programmer determines whether the device is part of the system, what it's group and type is, and whether it is able to modify the device.

U.S. Pat. No. 5,891,178 to Mann et al, describes a program or system and associated methods for rapidly evaluating and programming an implanted cardiac device. Specifically, the invention relates to an improved pacemaker programmer and diagnostic system for retrieving information stored within a pacemaker to be analyzed in real time. The information stored in the pacemaker is retrieved by means of a telemetric communication link. The system automatically identifies significant patient events such as regions of increased heart rate or loss of atrial or ventricular capture. In display, significant events are automatically identified so that the monitoring physician need not scroll through the retrieved data to identify significant events. Further, the system automatically suggests modifications to pacemaker parameters based upon certain retrieved data. The physician need only confirm the changes in order to modify the parameters within the pacemaker so that the modification of Smaker parameters is reduced to a one step process. The system also includes features for allowing the physician to interactively adjust program parameters while viewing those parameter changes in real time.

PCT publication WO00/38575 to Miesel et al discloses a non-invasive cardiac monitoring system and method with communications interface. Specifically, the invention relates to a system and method for determining a patient's cardiac output in a non-invasive manner and transmitting cardiac output data to remote host processor, communication system or a local output device. The system utilizes an implanted medical device coupled to an oxygen sensor, the oxygen sensor provides venous oxygen saturation data to the implantable medical device. The oxygen consumption unit produces oxygen consumption data using air exhaled by a patient. A processing unit calculates a cardiac output result in real time using the venous oxygen saturation data, the oxygen consumption data and arterial oxygen saturation data assumed to be about 100% or acquired using a sensor external to the patient. The interface may include a modem, a computer interface, a network interface or communication system interface, for example. The processing unit may communicate the cardiac output result to the remote host processor in an analog, digital or optical form.

U.S. Pat. No. 6,088,618 to Kerver discloses a pacemaker system and method for providing manual display concurrent with pacemaker software modification. The invention relates to a programmable pacemaker who is a programmer that has the capability of making software control modifications to one or more of pacemaker types that can be software modified to different control functions. The program queries manual data relating to the manual corresponding to each pacemaker type. Whenever a new control software release is loaded into the programmer, an accompanying new manual portion is also loaded into programmer memory. The programmer can then determine what manual portion or portions are superseded in the new control software is downloaded into any one of the respective different test maker types of the family.

A further limitation of the prior art relates to the management of multiple medical devices in a single patient. As indicated hereinabove, advances in modern patient therapy and treatment have made it possible to implant a number of devices in a patient. For example, an IMD such as a defibrillator, a neural implant, a drug pump, a separate physiologic monitor, and various other IMDs may be implanted in a single patient. To successfully manage the operations and assess the performance of each device in a patient with multiple implants, require continuous updates and monitoring of the devices. Further, it may be preferred to have an operable communication between the various implants to provide a coordinated clinical therapy to the patients.

Thus, there is a need to monitor the IMDs including a programmer on a regular, if not continuous, basis to ensure optimal patient care. In this regard, a graphical user interface (GUI) that integrates various static and animated images of the heart, and the implantable medical device would provide significant advances over the prior art. Specifically, by using enabling software in conjunction with a graphical user interface transfer of medical and device information to remote sites via the Internet, Intranet, Extranet, World Wide Web or other medium, monitoring and management of chronic patients could be enhanced. More specifically, using an instrument that may be placed in a patient's home the GUI of the present invention in combination with enabling software, could provide global connection and communication between patients and healthcare providers to monitor and manage the implantable devices remotely on a continuous basis.

SUMMARY OF THE INVENTION

The present invention discloses a GUI to illustrate various images and data. The GUI and associated software enable interactivity via a menu bar and/or a pointer pen. Pointing by the pen to a relative part of the GUI opens further menus. Yet another aspect of the invention includes a GUI implemented by integrating softwares to provide additional features into an instrument such as a programmer. Specifically, features relating to point interrogation and quick look screen displays to provide users menus that would enable them to view illustrations and images of the heart, the implantable medical device, and various other parameters. An additional aspect of the invention includes the use of a highly diverse software network system incorporated with the GUI to transport information to a patient station, remote station and expert stations such as a clinical care provider using a dedicated software. The implementation may preferably use Jini as a way to make applets move transparently across networks regardless of the type of connection deployed.

Yet another aspect of the invention relates to implementation of various communication systems to transfer the GUI illustrations to remote stations on a real time basis. For example, ECG analysis relating to exact heart rhythm, visualization and animation may be transmitted to a remote location via the internet, intranet, extranet or other equivalent medium, for remote viewing by physicians and caregivers.

The invention enables remote chronic management of one or more devices implanted in one or more patients by providing critical images for purposes of review and evaluation on a continuous basis.

DETAILED DESCRIPTION OF THE DRAWINGS

Figure 1A:
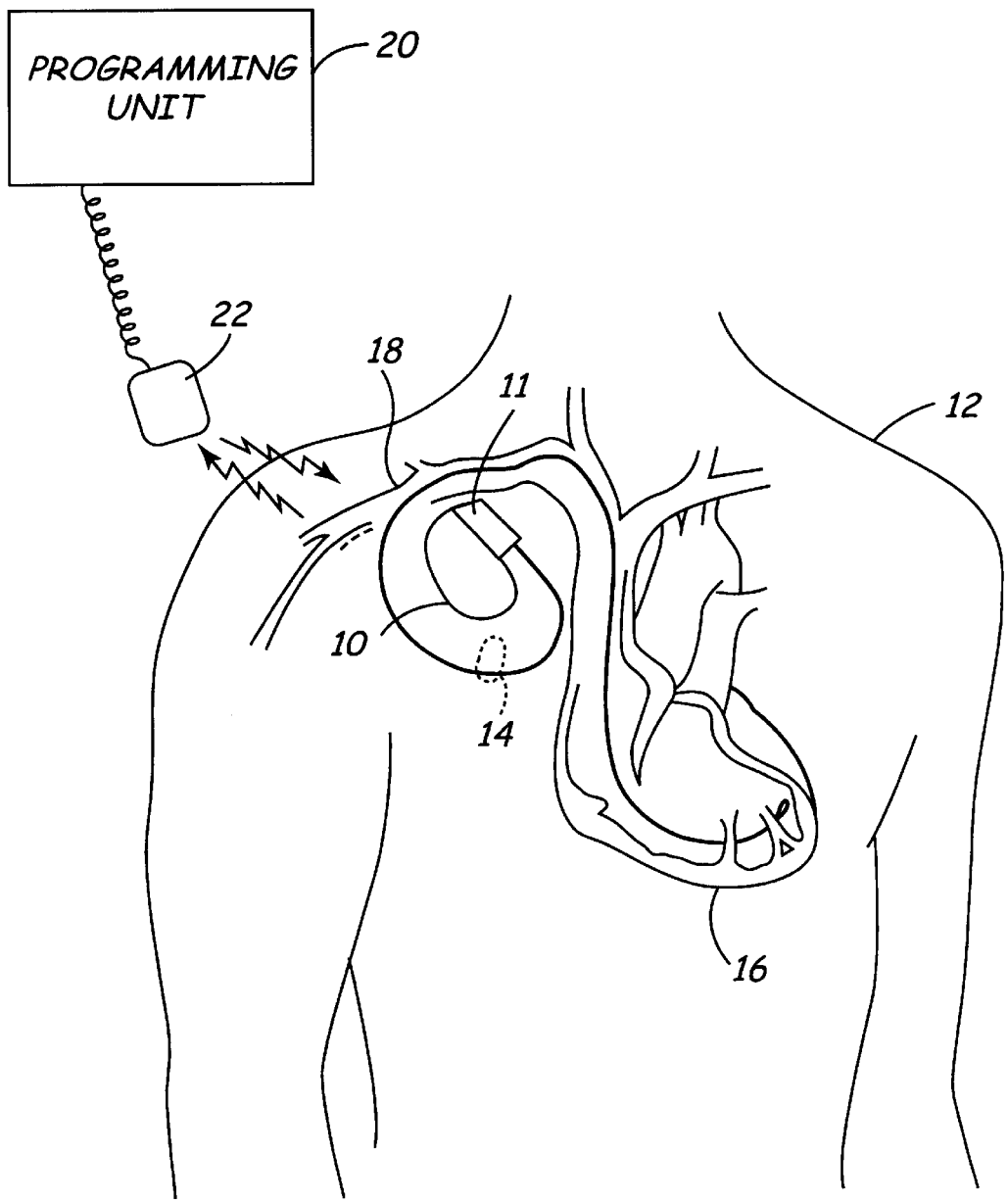
FIG. 1A is an illustration of a body implantable device system in accordance with the present invention, including hermetically sealed device e implanted in a patient and an external programming unit.

FIG. 1 is an illustration of an implantable medical device system adapted for use in accordance with the present invention. The medical device system includes an IMD 10 implanted in a patient 12. A ventricular pacemaker lead 14 is electrically coupled to pacemaker 10 in a conventional manner and extends into the patient's heart 16 vein 18. Near the distal end of lead 14 are one or more conductive electrodes for receiving electrical cardiac signals and/or for delivering electrical pacing stimuli to heart 16. Also depicted in FIG. 1 is an external programming unit 20 for non-invasive communication with implanted device 10 via uplink and downlink communication channels. Associated with programming unit 20 is a programming head 22 for facilitating two-way communication between implanted device 10 and programmer 20.

Figure 1B:
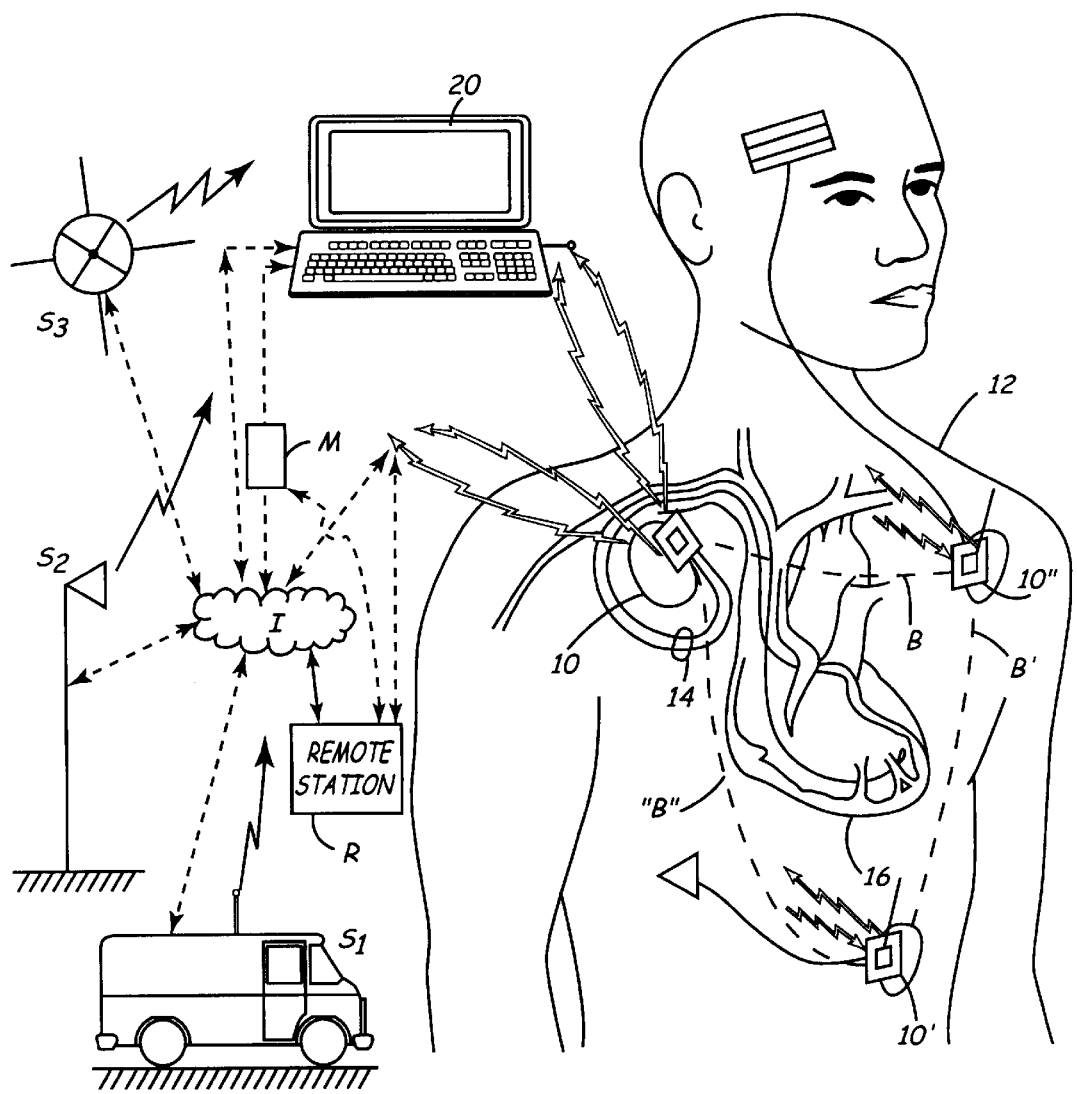
FIG. 1B is an illustration of a multi-implantable medical device system in accordance with the present invention, including various implanted medical devices in a patient having internal communications therein and also being communicable via instrumentation to provide remote monitoring and communications.

FIG. 1B is an alternate embodiment of FIG. 1A wherein several implantable medical devices, for example 10, 10' and 10" are implanted in patient 12. The devices may have internal communication within (B, B' and B") patient 12 and individual telemetric communication with programmer 20. In the alternate, the devices may have a common communication channel with programmer 20. Several other communication systems are disclosed wherein telecommunications could be implemented to provide a wireless communication between various stationary and mobile stations. For example, S1, S2, S3 represent a mobile station, a stationary station and a satellite system respectively. The system may also enable direct communication between programmer 20 and the Internet via modem M to enable access by physicians and care givers remotely.

Figure 2:
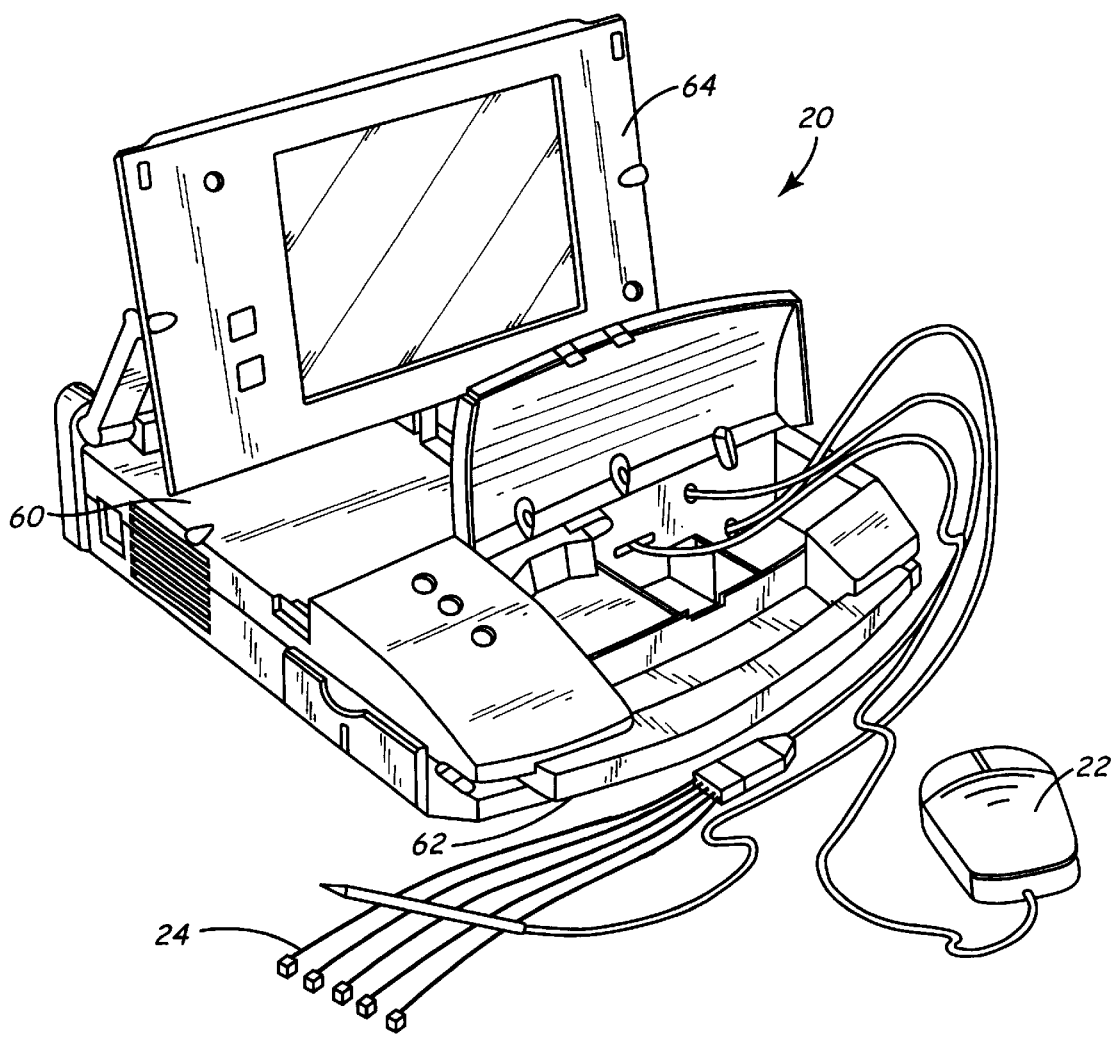
FIG. 2 is a perspective view of an external programming unit of FIG. 1A and FIG. 1B.

FIG. 2 is a perspective view of an instrument or programmer 20 in accordance with the presently disclosed invention. Internally, programmer 20 includes a processing unit not shown in the figure that, in accordance to the presently disclosed invention, is a personal computer type motherboard, for example, a computer mother board including a microprocessor such as an Intel Pentium III and related circuitry such as digital memory. The details of design and operation of the programmer's computer system will not be set forth in detail in the present disclosure as it is believed that such details are well known to those of ordinary skill in the art. Still referring to FIG. 2, programmer 20 includes an outer housing 60 and a carrying handle 62 so programmer 20 can be carried like a briefcase. An articulating display screen 64 is disposed on the upper surface of housing 60. As would be appreciated by those of ordinary skill in the art, display screen 64 is operatively coupled with computer circuitry disposed within housing 60 and is adapted to provide a visual display of graphics and/or data under the control of the antenna computer. As would be appreciated by those of ordinary skill in the art, it is often desireable to provide a means for determining the status of the patient's conduction system. Normally, programmer 20 is equipped with external ECG leads 24. In accordance with the present invention, programmer 20 is equipped with an internal printer (not shown) so that a hard copy of the patient's ECG or of graphic displays on the programmer's display screen 64 can be generated.

Several types of printers, such as the AR100 printer, available from General Scanning Company are known and commercially available to work with programmer 20. Programmer 20 described herein with reference to FIG. 2 is disclosed in more detail in U.S. Pat. No. 5,345,362, issued to Thomas J. Winkler, entitled "PORTABLE COMPUTER APPARATUS WITH ARTICULATING DISPLAY PANEL", which patent is hereby incorporated herein by reference in its entirety. The Medtronic Model 9790 Programmer is an implantable device programming unit with which the present invention may be practiced.

Figure 3:
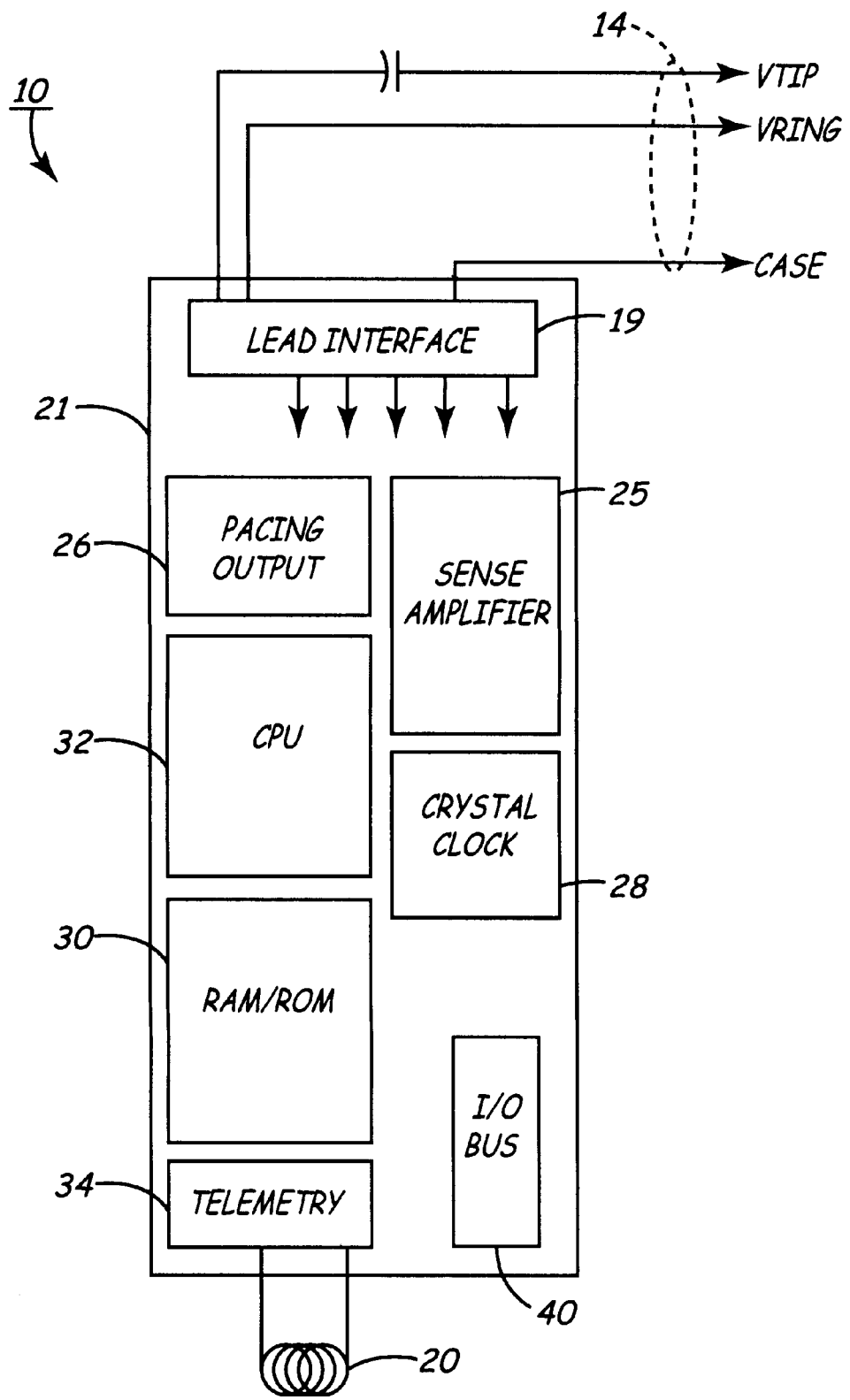
FIG. 3 is a block diagram of a typical implanted device of FIG. 1A or FIG. 1B.

FIG. 3 is a block diagram of the electronic circuitry that makes up pulse generator 10 in accordance to the presently disclosed invention. As can be seen from FIG. 3, generator 10 comprises a primary simulation control circuit 21 for controlling the device's pacing and sensing functions. The circuitry associated with stimulation control circuit 21 may be of conventional design in accordance, for example, with what is disclosed in U.S. Pat. No. 5,052,388 issued to Sivula et al, entitled "METHOD AND APPARATUS FOR IMPLEMETNING ACTIVITY SENSING IN A PULSE GENERATOR". To the extent that certain components of pulse generator 10 are conventional in their design and operation, such components will not be described herein in detail, as it is believed that design implementation of these components would be a matter of routine to those of ordinary skill in the art. For example, stimulation control circuit 21 of FIG. 3 includes stimulating pulse output circuit 26, a crystal clock 28, random access memory and read only memory (RAM/ROM) unit 30 and a central processing unit (CPU) 32, all of which are well known in the art. Pacemaker 10 also includes internal communication circuit 34 so that it is capable of communicating with internal programmer/control unit 20 as described in FIG. 2 in greater detail. Specifically circuit 34 relating to telemetry, the particular focus to the present invention because most of the wireless communication system and the schemes implemented by the present invention are interfaced with the implanted medical device via this internal communication circuit 34.

With continued reference to FIG. 3, pulse generator 10 is coupled to one ventricular lead 14 which, when implanted, extends transvenously between the implant site of post generator 10 and the patient heart 16 as previously noted with reference to FIGS. 1A and 1B. Physically, the connections between lead 14 and the various internal components of post generator 10 are facilitated by means of a conventional connector block assembly 11 shown in FIG. 1. Electrically, the coupling of the conductors of lead 14 and internal electrical components of pulse generator 10 may be facilitated by a lead interface circuit 19 which functions in a multiplexor like manner to selectively and dynamically establish necessary connections between various conductors and leads 14 including ventricular tip and ring electrode conductors and individual electrical components of post generator 10 as is familiar to those of ordinary skill in the art.

For the sake of clarity, the specific connections between lead 14 and the various components of post generator 10 are not shown in FIG. 3, although it will be clear to those of ordinary skill in the art. For example, that lead 14 will necessarily be coupled either directly or indirectly to sense amplifier circuitry 25 and the simulating pulse output circuit 26 in accordance with common practice such that cardiac electric signals may be conveyed to sensing circuitry 25 to enable the delivery of stimulating pulses to cardiac tissue via leads 14. Also not shown in FIG. 3 is protection circuitry commonly included in implanted devices to protect, for example, the sensing circuitry of the device from high voltage stimulating pulses. Stimulating control circuit 21 includes central processing unit 32 which may be an off-the-shelf microprocessor or microcontroller, but in the present invention could be a custom integrated circuit. Although specific connections between CPU 32 and other components of stimulation control circuit 21 are not shown in FIG. 3, it should be apparent to those skilled in the art that CPU 32 functions to control the timed operation of stimulating pulse output circuit 26 and sense amplifier circuit 25 under control of programming stored in RAM/ROM unit 30. It is believed that those of ordinary skill in the art will be familiar with such an operative structure and arrangement. With continued reference to FIG. 3, crystal off letter 28 provides mean timing cross signals to stimulation control circuit 21. Again, the lines over which such crossing signals are provided to the various timed components of pulse generator 10 are omitted from FIG. 3 for the sake of clarity. It is to be understood that the various components of post generator 10 depicted in FIG. 3 are powered by means of a batter that is contained within the hermetic enclosure of pacemaker 10 in accordance with common practice in the art. For the sake of clarity in the figures, the battery and the connections between it and the other components of post generator 10 are not shown. Stimulating post output circuit 26, which functions to generate cardiac stimuli under control of signals issued by CPU 32 may be, for example, of the type disclosed in U.S. Pat. No. 4,476,868 to Thompson, entitled "BODY STIMULATOR OUTPUT CIRCUIT", which patent is hereby incorporated by reference in its entirety. Again, however, it is believed that those of ordinary skill in the art could select from many different types of prior art pacing output circuits that would be suitable for purposes of practicing the present invention.

Sense amplifier circuit 25 functions to receive electrical cardiac signal from ventricular lead 14 and to process such signals to derive event signals reflecting the occurrence of a specific cardiac electrical event. CPU 32 provides this event indicating signal for use in controlling the synchronous stimulating operation of post generator 10 in accordance with common practice in the art. In addition, this event indicating signals may be communicated by an uplink transmission to external programming unit 20 for visual display to a physician or clinician. Those of ordinary skill in the art will appreciate that pacemaker 10 may include numerous other components and systems. For example, activity sensors and associated circuitry. The presence or absence of such additional components in pacemaker 10, however, is not believed to be pertinent to the present invention which relates primarily to the implementation or remote communication, preferably via circuitry 25 in pacemaker 10 and associated communications in external units such as programmer 20.

Figure 4A:
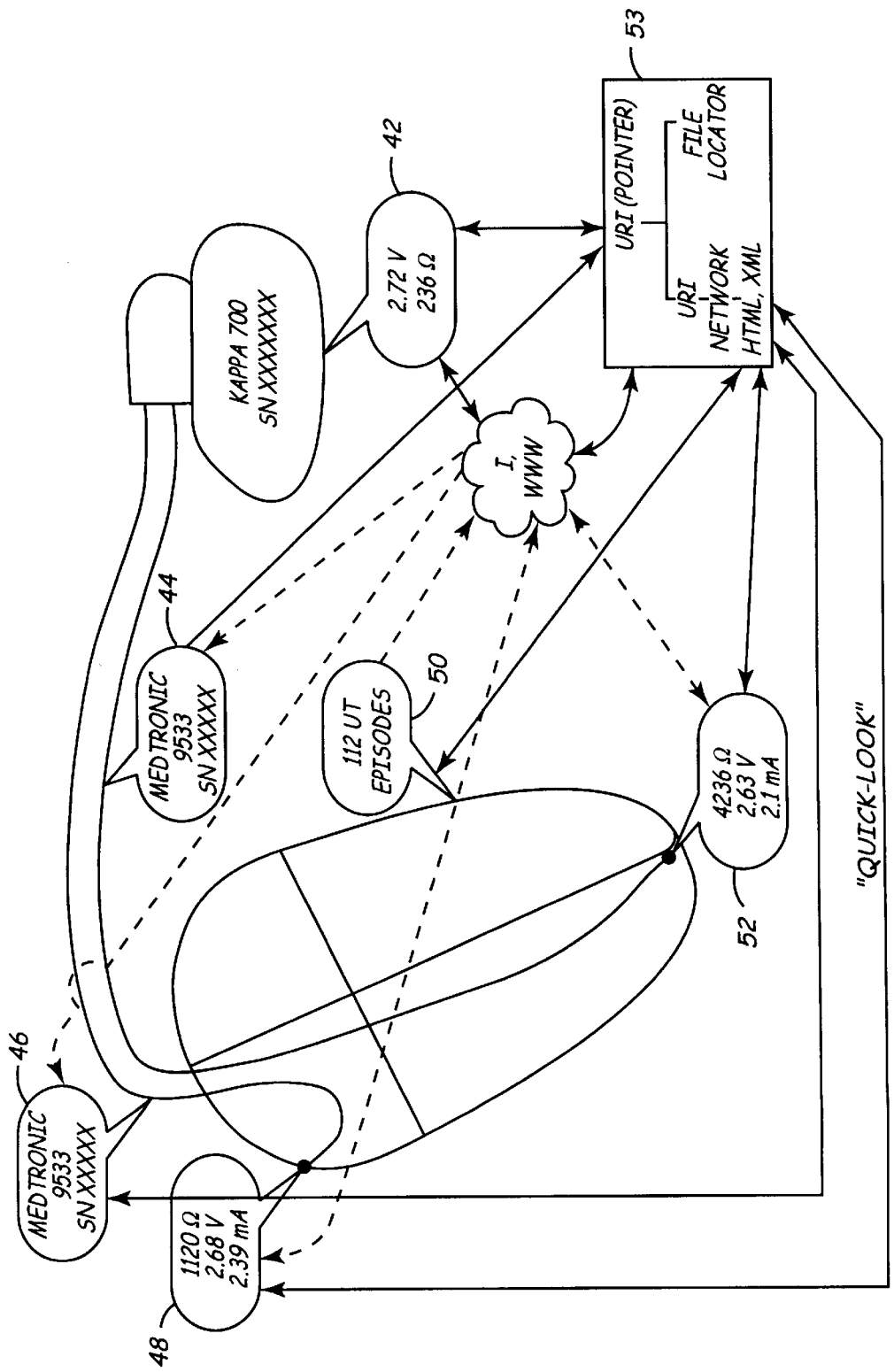
FIG. 4A is a graphical user interface representation of an implanted medical device and a heart with graphic text balloons for accessing and reviewing various structures and parameters.
Figure 4B:
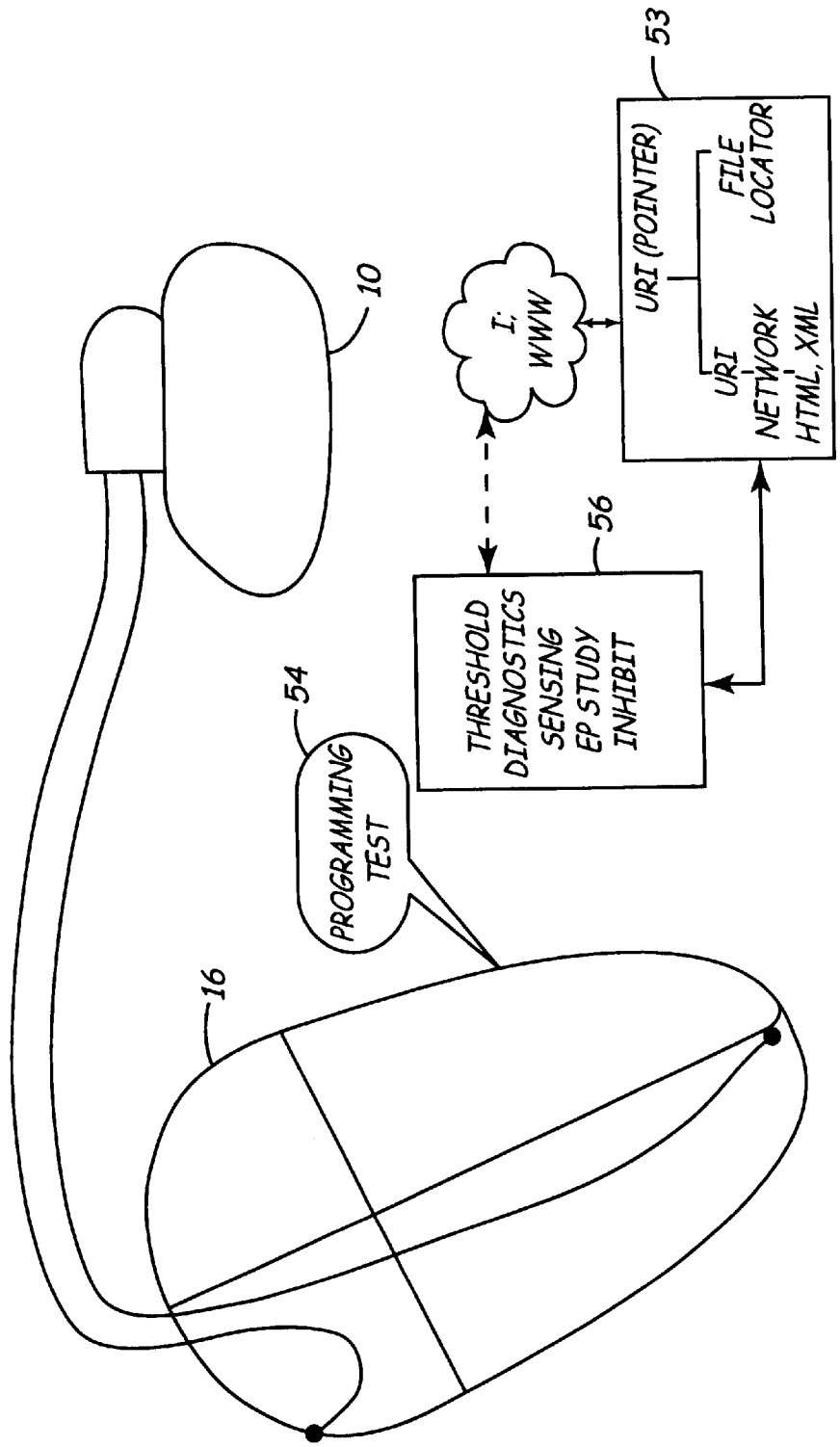
FIG. 4B is a variation of FIG. 4A wherein a ventricular channel menu is highlighted or selected for review.

FIG. 4A is a an illustration of a GUI display in accordance with the present invention. Specifically, upon interrogation by an instrument such as programmer 20, a quick look screen such as one displayed in FIG. 4A appears. As can be seen, the screen illustrates an integrated system in which implanted medical device 10 and heart 16 are shown. Further, various balloons, including balloon 42 depicting information relating to medical device 10, balloon 44, relating to information of ventricular lead, balloon 46 with atrial lead information, balloon 48 representing pacing lead specification, balloon 50 relating to cardiac episodes and balloon 52 relating to pacing lead specification, are shown for example. It should be understood that various other balloons may be added using the graphical user interface and software of the present invention. In accordance with the present invention, the image of heart 16 and pacing leads are depicted exactly in the current position of implant. The image of the IMD 10 includes exact label including the serial number. The layered menus (such as shown in FIG. 4B) are preferably designed as graphic text balloons. The layered architecture enables to access detailed information on a component or cardiac parameter. For example, under IMD 10 pointing on balloon 42 would yield another graphic on battery information. "Battery OK" message is displayed first, if in fact, the battery is normal. Pointing at the "Battery OK" balloon will further display existing battery parameters. Similarly, balloons 46, 48 and 52 could be activated to reveal further information on lead and electrode parameters. Balloon 50 may be activated to reveal either a static or dyanic image of heart 16. Real time depolarization wave forms are reviewed under balloon 50 and subsets thereof. The system of the present invention enables animation to be synchronized with real time measured ECG waveform recorded by programmer/instrument 20.

In an alternate embodiment, icon-suited to the programming menu is offered within an opened balloon. Thus, for example, achieving a region at the sinus node would open a pacing note management menu. Similarly, activating a region at the A-V note would open the A-V delay management menu. Further, activating a ventricular muscle region could open-the ventricular channel programming. Activation of the ventricular lead would open the lead and threshold menu.

Referring now to FIG. 1B, in further reference to FIGS. 4A and 4B, the present invention is implemented on instrument or programmer 20. Programmer 20 includes telemetry or wireless communications with one or more medical devices 10, 10' and 10" in patient 12. Upon interrogation of one or more of the medical devices (10, 10' and 10"), a quick look display will appear on the screen of instrument 20. The quick display includes an image of the heart and one or more images of implantable medical devices 10, 10' and 10" in the same GUI. Heart image 16 comprises images of implanted leads associated with balloon information's 44 and 46. This lead represents exact position in heart 16. The image of one or more implanted devices, 10, 10', 10", includes the serial number of the devices. The GUI of the present invention is more than just displaying pictures.

FIG. 4A represents a graphical display sample in accordance with the present invention. Such a sample may be displayed at instrument or programmer 20. The display may include enabling software 53 which would have URI or pointer that will enable access to Internet I through a URL and a network with a proper protocol. In the alternate, the URI image points to the file locator. Generally, the display might show one or more implantable devices such as IMD 10, 10' and 10" displaying the serial number of the implant. A pointing device such as a trackball, mouse or pen is used to interact with the displayed images. Selecting balloon 42 will enable a review of the electrical standards for implanted device 10. Further, under balloon 42, there is a layered set of graphics to guide the user to various information regarding the specification of device 10. Further, implementing enabling software 53 via URL, the user may access a network that is web enabled to operate with the internet, intranet, extranet or world wide web to access relevant information about the device from a Medtronic server.

In the alternate, the user may point the URI to access a file locator that may contain the specific device information relevant to the display. Similarly, the user might point to balloons 44 or 46 to find the serial number of the leads. Furthermore, the user might highlight balloons 48 and/or 52 to find information and specifications about the electrodes. As depicted in the figures, all the balloons, whether the lines are indicated or otherwise, would have a URI pointer that would enable access to the internet, worldwide web, intranet, extranet or similar other network supported by a protocol. Further, any of the displays may be transmitted to a remote station via the internet, intranet, extranet or world wide web.

Referring now to FIG. 4B, pointing at programming test balloon 54 would yield a subset of menus 56 that is further defined under each of the headlines for the reviewer to review. The information could also be transferred to a network such as internet, extranet, intranet, worldwide web, using enabling software 53.

Accordingly, the present invention provides a medical device GUI for cardiac electrophysiology animation and display in combination with displays and information relating to the implanted medical device. Further, the invention enables data transfer and communications between one or more medical devices implanted in one or more patients and a remote clinic via an instrument such as a programmer including a GUI with enabling software using the Internet or other network system.

It is to be understood that the GUI structure and software of the present invention provide both real-time and recorded data of implanted medical device information, including leads and electrodes implanted in one or more patients. The software scheme and the GUI design advanced in the present invention enable physicians and caregivers to visually access, inspect and assess implanted medical device, information and data, thus enabling remote patient monitoring and communication systems.

It is to be understood that the above description is intended to be illustrative and not restrictive, meaning other embodiments would be apparent to those of skill in the art upon reading and understanding the above description. Scope of the invention should therefore be determined with reference to the appended claims along with the full scope of equivalents to which such claims are entitled.

What is claimed is:

1. A graphical user interface (GUI) for interacting with displays presented on a medical instrument in data communications with one or more implantable medical devices (IMDS) in one or more patients, the GUI in combination with the medical instrument comprising:

means for visually displaying said one or more IMDs in said one or more patients; and means for generating said displays;

said GUI being implemented in layered menus provided as graphic text balloons to permit paging through various displays to access detailed information relating to said one or more IMDs;

said layered menus including access to a remote station.

2. The GUI and medical instrument of claim 1 wherein said displays include images representing cardiac electrophysiology data relating to said one or more IMDs in said one or more patients.

3. The GUI and medical instrument of claim 1 wherein said means for visually displaying includes a screen or said medical instrument.

4. The GUI and medical instrument of claim 1 wherein said GUI includes a subset of display menus.

5. The GUYI and medical instrument of claim 4 wherein the GUI implements an enabling software to exchange data with a remote server.

6. The GUI and medical instrument of claim 5 wherein said enabling software further includes links to a network system.

7. The GUI and medical instrument of claim 6 wherein said network is selected from the list consisting of LAN, WAN, WWW, Internet, Intranet and Extranet.

8. A graphical user interface (GUI) for interacting with displays presented on a medical instrument in data communications with one or more implantable medical devices (IMDs) in one or more patients, the GUI in combination with the medical instrument comprising:

means for visually displaying said one or more IMDs in said one or more patients; and means for generating said displays;

said GUI being implemented to navigate through various layers of said displays relating to said one or more IMDs in said one or more patients;

said GUI implements an enabling software that exchanges data with a remote server and that includes links to a network system selected from a list consisting of LAN, WAN, WWW, Internet, Intranet, and Extranet;

said GUI including a subset of display menus that includes a HTML menu to connect to said WWW network, said Internet and said Intranet.

9. A graphical user interface (GUI) for interacting with displays presented on a medical instrument in data communications with one or more implantable medical devices (IMDs) in one or more patients, the GUI in combination with the medical instrument comprising:

means for visually displaying said one or more IMDs in said one or more patients; and means for generating said displays that include animated images;

said GUI being implemented to navigate through various layers of said displays relating to said one or more IMDs in said one or more patients.

10. A cardiac electrophysiology display and data communications system for displaying virtual static and animated images of one or more patients with one or more implanted medical devices (IMDs) including a GUI implemented to navigate through various layers of images, the system comprising:

an instrument in data communication with the IMDs;

at least one screen for one said instrument to display the images; and the GUI implemented in layered menus as graphic text balloons to permit paging through various images for display in said at least one screen;

the GUI having one menu for activation to reveal either a static or a dynamic image of the heart; and the GUI providing for display of a real time depolarization waveform for review and synchronization of an animated dynamic image of the heart with the waveform.

11. The system of claim 10 wherein said data communication includes enabling software to access a server.

12. The system of claim 11 wherein said enabling software includes remote data transfer and exchange via a network system.

13. The system of claim 12 wherein said network system includes a LAN, WAN, WWW, Internet and Intranet.

14. The system of claim 10 wherein said data communication includes enabling software to access a LAN, WAN, WWW, Internet and Intranet.

15. The system of claim 10 wherein the images include a subset of display menus.

16. A cardiac electrophysiology display and data communications system for displaying virtual static and animated images of one or more patients with one or more implanted medical devices (IMDs) including a GUI implemented to navigate through various layers of images, the system comprising:

an instrument in data communication with the IMDs;

at least one screen for one said instrument to display the images; and the GUI implemented to navigate through the layers of the images for display in said at least one screen;

said images including a menu to connect to related information and data on the Internet.

17. A cardiac electrophysiology display and data communications system for displaying virtual static and animated images of one or more patients with one or more implanted medical devices (IMDs) including a GUI implemented to navigate through various layers of images, the system comprising:

an instrument in data communication with the IMDs;

at least one screen for one said instrument to display the images; and the GUI implemented to navigate through the layers of the images for display in said at least one screen;

the static and animated images being provided in a quick look display.

* * * * *